United States Patent [19]

Yamaguchi et al.

[11] 3,957,973

[45] May 18, 1976

[54] COMPOSITION AND METHOD FOR GASTRIC ULCER-PREVENTION AND PICA-PREVENTION OF SWINE

[75] Inventors: Masahide Yamaguchi, Tochigi; Kanemichi Sasaki, Kasukabe, both of Japan

[73] Assignees: Nippon Kayaku Kabushiki Kaisha, Tokyo; Glico Chikusan Kabushiki Kaisha, Kuroiso, both of Japan

[22] Filed: July 19, 1974

[21] Appl. No.: 490,089

Related U.S. Application Data

[63] Continuation-in-part of Ser. No. 320,850, Jan. 4, 1973, abandoned.

[30] Foreign Application Priority Data

Jan. 14, 1972 Japan.................................. 47-6475
June 20, 1972 Japan.................................. 47-61683

[52] U.S. Cl. ................................................. 424/81
[51] Int. Cl.² ......................................... A61K 31/78

[58] Field of Search ........................................ 424/81

[56] References Cited
UNITED STATES PATENTS 3,215,604   11/1965   Biamonte............................. 424/81

FOREIGN PATENTS OR APPLICATIONS 45-155   6/1970   Japan.................................. 424/81

OTHER PUBLICATIONS

Chemical Abstracts, Vol. 61, 8565; 12545, (1964).

*Primary Examiner*—Frederick E. Waddell
*Attorney, Agent, or Firm*—Schuyler, Birch, Swindler, McKie & Beckett

[57] ABSTRACT

A gastric ulcer- and pica-preventing method of swine comprising continuously or repeatedly feeding sodium polyacrylate or potassium polyacrylate of average polymerization degree of not less than 15,000 to the swine in an amount of 0.05 to 1.5 % by weight of feed.

3 Claims, No Drawings

COMPOSITION AND METHOD FOR GASTRIC ULCER-PREVENTION AND PICA-PREVENTION OF SWINE

This application is a continuation-in-part of application Ser. No. 320,850 filed Jan. 4, 1973, now abandoned.

This invention relates to a method for preventing swine from gastric ulcer and pica to promote the growth of swine by continuously or repeatedly administering to the swine sodium polyacrylate or potassium polyacrylate of average polymerization degree of not less than 15,000 in admixture with a formula feed for swine.

With recent development of swine-raising using formula feeds, a formula feed excellent in feed efficiency has come to be required. Such formula feed excellent in feed efficiency is a feed of high nutritive value which has been lowered in content of crude fiber, and hence has been a direct or indirect cause for inhibiting the growth of swine due to gastric ulcers and the gastric lesions and pica. That is, when swine are raised with only formula feeds without using litters, they frequently suffer from gastric ulcers. Gastric ulcers of swine occur chiefly at the esophageal areas of their stomachs, with the result that swine which are serious in degree of disease die, and even those which are slight in degree of disease are considerably inhibited in growth.

Further, when raised by group feeding, swine cause such pica called tail-biting, and bite or eat off tails of the other swine. Among the thus damaged swine, those which have been seriously damaged die from excessive bleeding or from infection with bacteria, and even those which have been slightly damaged undergo considerable stress and hence are inhibited in growth. Although a counter-measure therefor can be accomplished by adoption of artificial docking at the pigling stage of swine, there are such drawbacks that much labor is required in said docking and the swine have no tails sufficient in length which are useful for moving the swine when they have grown.

The above-mentioned gastric lesion and pica of swine are frequently observed in swine which have been fed with formula feeds less in content of crude fiber, and are chiefly ascribable to feeding with formula feeds high nutritive value and excellent in feed efficiency. For prevention of the said diseases, there have been adopted such processes that in addition to formula feeds, crude feeds are used as litters or are so fed as to be freely eaten by the swine. These processes, however, are not practical in that feed efficiency of the formula feeds is lowered and the amount of faeces and manures is increased, and labor burden is increased in feeding the swine.

Thus, all the conventional processes for prevention of the above-mentioned diseases have many difficulties, and there is no good means which is connected to the form of feeds to be used on commercial scale, so that it is an urgent necessity to overcome the above-mentioned difficulties in some way by use of feed additives. On the other hand, antibiotics and the like substances have extensively been used as feed additives chiefly for growth promotion and diarrhea prevention. These additives, however, bring about such problems that they remain in the living body of swine and resistant bacteria are produced therein.

With an aim to solve the above-mentioned problems, the present inventors made extensive studies to find that when a polyacrylate such as sodium polyacrylate or potassium polyacrylate in admixture with a formula feed is administered to a swine, the swine is effectively prevented from gastric ulcer and from under-growth due to gastric ulcer and pica, and thus is greatly promoted in growth. Based on the above finding, the inventors have accomplished the present invention.

The average polymerization degree of polyacrylates used in this invention is 15,000 or more. The higher the polymerization degree of polyacrylates is, the better the effects of gastric ulcer prevention and pica prevention are, as shown in the following Experimental Example. Experimental Example (Effects of acrylate and polyacrylate on pigs)

1. Test method:
    1.
        1. Test period: 90 days
        2. Test swine: 100 Landrace pigs of about 30 kg in body weight were divided into five sections, each section consisting of 10 female pigs and 10 castrated male pigs. All the pigs were healthy ones raised by giving a small amount of a crude feed every day and spreading rice straw as a litter.
        3. Feed and test sections: As the basal feed was used a practical powdery formula feed. The pigs of 4 test sections (treated sections) were fed with the basal feed incorporated with 0.2 % sodium acrylate or 0.2 % sodium polyacrylate (hereinafter abbreviated to PANA) having average polymerization degree of 5,000 to 14,500, 15,000 to 25,000 and 60,000 to 80,000 respectively, and pigs of one section (control section) were fed with only the basal feed. The components and composition of the basal feed were as set forth in Tables 1 and 2, respectively, and the classification of the test sections was as set forth in Table 3.

Table 1

| Components of feed: | |
|---|---|
| Maize-milo mixture | 70 % |
| Soybean oil meal-fish meal mixture | 20 % |
| Molasses | 2 % |
| Tallow | 2 % |
| Rice bran-alfalfa meal mixture | 4 % |
| Vitamin-mineral premix | 2 % |

Table 2

| Composition of feed: | | | |
|---|---|---|---|
| Crude protein | Crude fat | Crude fiber | Crude ash |
| 15.8 % | 5.0 % | 2.4 % | 4.7 % |

Table 3

| Section | Classification of test sections: | | | | Control section |
|---|---|---|---|---|---|
| | Section 1 | Treated Section | | | Section 5 |
| | | Section 2 | Section 3 | Section 4 | |
| Additive | 0.2 % sodium acrylate | 0.2 % PANA of A.P.D. of 5,000 – 14,500 | 0.2 % PANA of A.P.D. of 15,000 – 25,000 | 0.2 % PANA of A.P.D. of 60,000 – 80,000 | None |

(A.P.D. refers to average polymerization degree.)

4. Feeding method: Each 20 pigs were raised in a concrete floor pen of 2.7 m × 7.2 m in area with self-feeding, non-litter and free water-drinking.

Test results:

The state of esophageal area of the stomach of each swine slaughtered and anatomized on the 90th day was as shown in Table 4.

In the control section and the sodium acrylate section 1, the outbreak of ulcer was observed, while in the sodium polyacrylate sections 3 and 4 using PANA having A.P.D. of 15,000 or more, the outbreak of ulcer was not observed. Particularly, the section 4 using PANA having highest A.P.D. showed the most excellent effect. The section 2 using PANA having A.P.D. of 5,000 – 14,500 was better in antiulcer effect than the section 1 using sodium acrylate but worse than the section 3. Accordingly, it was found that the polyacrylates having A.P.D. of 15,000 or more (1,410,000 or more in molecular weight) are effective in practical use.

Table 4

| Section | | Treated Section | | | | Control section |
|---|---|---|---|---|---|---|
| | | Section 1 | Section 2 | Section 3 | Section 4 | Section 5 |
| Normal | | 0 | 0 | 2 | 5 | 0 |
| Lesion | Parakeratosis + | 1 | 3 | 5 | 9 | 1 |
| | Parakeratosis ++ | 1 | 12 | 11 | 6 | 2 |
| | Erosion | 11 | 3 | 2 | 0 | 9 |
| | Ulcer | 7 | 2 | 0 | 0 | 8 |

The lesions were classified according to the following standards:
Parakeratosis +: Slight parakeratosis on pavement epithelium
Parakeratosis ++: Advanced parakeratosis on pavement epithelium
Erosion: Partial decay of pavement epithelium
Ulcer: Decay of epithelium and exposure of tunica muscularis For gastric ulcer prevention and pica prevention of swine, a definite amount of sodium polyacrylate or potassium polyacrylate powder is mixed as a feed additive with, for example, such a feed as set forth in Table 1 of Experimental Example, above, and the resulting powdery feed is administered either as it is or after forming the polyacrylate-containing feed into pellets or crumbles by use of a pelletizing machine according to an ordinary procedure. The administration amount of the polyacrylate according to the present invention varies depending on the state and body weight of swine, but is ordinarily 0.05 to 1.5 % by weight based on the weight of the feed, and the resulting polyacrylate-containing feed is continuously or repeatedly fed to swine.

This invention is illustrated in detail below with reference to examples.

EXAMPLE 1

1. Test method:
   1. Test period: 99 days
   2. Test swine: 45 Landrace × Hampshire pigs (half male and half female) of about 33 kg in body weight. These pigs were divided into 3 sections.
   3. Feed and test sections: As the basal feed was used a practical powdery formula feed comprising the same components as in Table 1 of Experimental Example. The pigs of 2 test sections (treated sections) were fed with the basal feed incorporated with PANA having average polymerization degree of 40,000 to 60,000 in proportions of 0.3 % and 15,000 to 25,000 in proportions of 0.1 %, respectively, and the pigs of one section (control section) were fed with only the basal feed. The composition of the basal feed were as set forth in Table 5, and the classification of the test sections was as set forth in Table 6.

Table 5

| | Composition of feed: | | |
|---|---|---|---|
| Crude protein | Crude fat | Crude fiber | Crude ash |
| 16.1 % | 4.8 % | 2.6 % | 5.0 % |

Table 6

| Section | Classification of test sections: | | Control section |
|---|---|---|---|
| | Treated section | | |
| | Section 1 | Section 2 | Section 3 |
| Additive | 0.3 % PANA | 0.1 % PANA | None |

4. Feeding method: Each 15 pigs were raised in a solid floor pen of 2.7 × 7.2 m in area with self-feeding, non-litter and free water-drinking.

2. Test results:

The growth state of the swine of each section was as set forth in Table 7. On the 80th day after initiation of the test, the test swine was clinically observed to find that one of the swine of the control section (section 3) has been afflicted with gastric ulcer. Accordingly, the said swine was culled and anatomized to confirm that the swine had bled due to great ulcer. The state of esophageal area of the stomach of each swine at the time of slaughter was as set forth in Table 8. Both the sections 1 and 2 in which had been used the basal feed incorporated with PANA showed good growth states and particularly, both the average body weight increases per day in the treated sections were 11 % or more larger than that in the control section, as set forth in Table 7. Further, the feed conversion ratios were also improved. That is, 2 normal swine and 1 normal swine were observed respectively in the sections 1 and 2, in which had been used the basal feed incorporatd with 0.3 % and 0.1 % of PANA, respectively, whereas no normal swine was found in the control section. Further, in the treated sections, the degree of disease of each swine was at worst the stage of parakeratosis, whereas in the control section, substantially all of the swine had suferred from erosion and ulcer. Thus, a great difference was observed between the swine of the treated sections, in which PANA was used as additive, and those of the control section, in which no PANA was used.

Table 7

| (Average): Section<br>Item | Growth state (Average): | | Control section |
|---|---|---|---|
| | Treated section | | |
| | Section 1 | Section 2 | Section 3 |
| Body weight at the time of initiation of test | 33.0 kg | 34.1 | 33.4 |
| Body weight at the time of completion of test | 88.6 kg | 89.5 | 84.8 |
| Body weight increase during the test period | 55.6 kg | 55.4 | 51.4 |
| Average feeding days | 92.6 days | 90.7 | 96.4 |
| Average body weight increase per day | 600 g | 615 | 533 |
| Feed conversion ratio | 3.59 % | 3.63 | 3.70 |

Table 8

| | State of esophageal area of stomach: | | | Control section |
|---|---|---|---|---|
| Section | Treated section | | | |
| Item | | Section 1 | Section 2 | Section 3 |
| Normal | | 2 | 1 | 0 |
| | Para-keratosis + | 6 | 7 | 0 |
| | Para-keratosis ++ | 7 | 5 | 3 |
| Lesion | Erosion | 0 | 2 | 6 |
| | Ulcer | 0 | 0 | 6 |

The classification of the lesions is the same as in Experimental Example.

EXAMPLE 2

1. Test method:

1. Test period: 85 days
2. Test swine: 30 Pigs of Landrace and of the first filial generation of Landrace of about 41 kg in body weight were divided into 2 sections.
3. Feed and test sections: As the basal feed was used as practical powdery formula feed comprising the same components as in Table 1 of Experimental Example. The pigs of one test section (treated section) were fed with the basal feed incorporated with 0.2 % of potassium polyacrylate (hereinafter abbreviated to PAK) having average polymerization degree of 55,000 to 75,000. The composition of the basal feed was as set forth in Table 9, and the classification of test sections was as set forth in Table 10.

Table 9

| Composition of feed: | | | |
|---|---|---|---|
| Crude protein | Crude fat | Crude fiber | Crude ash |
| 16.2 % | 5.1 % | 2.9 % | 4.9 % |

Table 10

| Section | Classification of test sections: | |
|---|---|---|
| | Treated section | Control section |
| | Section 1 | Section 2 |
| Additive | 0.2 % PAK | None |

4. Feeding method: Each 15 pigs were raised in a solid floor pen of 3.6 × 4.5 m in area with selffeeding, non-litter and free water-drinking.

2. Test results:

The growth state of the swine of each section was as set forth in Table 11. The average body weight increase per day of the swine of the treated section as 704 g, whereas that of the swine of the control section was 646 g. As to the feed conversion ratio, a more or less difference was observed between the treated section and the control section. The state of esophageal area of the stomach of each swine was as set forth in Table 12. That is, 2 normal swines were observed in the treated section, whereas no normal swine but many swines advanced in lesion were observed in the control section.

Table 11

| Section<br>Item | Growth state (Average): | |
|---|---|---|
| | Treated section | Control section |
| Body weight at the time of initiation of test | 40.1 kg | 40.4 |
| Body weight at the time of completion of test | 93.5 kg | 89.6 |
| Body weight increase during the test period | 53.4 kg | 49.2 |
| Average feeding days | 75.8 days | 76.2 |
| Average body weight increase per day | 704 g | 646 |
| Feed conversion ratio | 3.30 % | 3.40 |

Table 12

| Item | State of esophageal area of stomach: | Treated section | Control section |
|---|---|---|---|
| | Section | | |
| Normal | | 2 | 0 |
| | Parakeratosis + | 10 | 4 |
| Lesion | Parakeratosis ++ | 3 | 5 |
| | Erosion | 0 | 5 |
| | Ulcer | 0 | 1 |

The classification of the lesions is same as in Experimental Example.

EXAMPLE 3

1. Test method:

1. Test period: 49 days
2. Test swine: 24 Pigs of about 45 kg in body weight were equally divided into 4 sections. The strains of pigs and classification of test sections were as set forth in Table 13. All the male pigs were castrated.

Table 13

| | | Strains of swine and classification of sections: | | | | |
|---|---|---|---|---|---|---|
| Treated section | Section 1 | Swine No. 1 – 304 ♂ | | Section 3 | Swine No. 13 – 322 ♂ | |
| | | Swine No. 2 – 311 ♂ | | | Swine No. 14 – 303 ♂ | |
| | | Swine No. 3 – 308 ♀ | | | Swine No. 15 – 320 ♀ | |
| | | Swine No. 4 – 317 ♂ | | | Swine No. 16 – 314 ♀ | |
| | | Swine No. 5 – 319 ♂ | | | Swine No. 17 – 310 ♀ | |
| | | Swine No. 6 – 313 ♂ | | | Swine No. 18 – 307 ♂ | |
| Control section | Section 2 | Swine No. 7 – 305 ♀ | | Section 4 | Swine No. 19 – 301 ♂ | |
| | | Swine No. 8 – 316 ♀ | | | Swine No. 20 – 324 ♀ | |
| | | Swine No. 9 – 321 ♂ | | | Swine No. 21 – 312 ♂ | |
| | | Swine No. 10 – 302 ♀ | | | Swine No. 22 – 315 ♀ | |
| | | Swine No. 11 – 323 ♀ | | | Swine No. 23 – 306 ♂ | |
| | | Swine No. 12 – 309 ♂ | | | Swine No. 24 – 318 ♂ | |

Strains:
301 – 304  (Landrace ♀ × Large Yorkshire ♂) ♀ × Hampshire ♂   Born on Nov. 26, 1971
305 – 308  Landrace ♀ × Hampshire ♂   Born on Dec. 1, 1971
309 – 316  Landrace ♀ × Large Yorkshire ♂   Born on Nov. 25, 1971
317 – 324  Landrace ♀ × Hampshire ♂   Born on Nov. 24, 1971

3. Feed and test sections: As the basal feed was used a practical powdery formula feed comprising the same components as in Table 1 of Experimental Example. The pigs of the sections 1 and 3 (treated sections) were fed with the basal feed incorporated with 0.5 % of PANA having average polymerization degree of 30,000 to 40,000, and the pigs of the sections 2 and 4 (control sections) were fed with only the basal feed. The composition of the basal feed was as set forth in Table 14, and the classification of the test sections was as set forth in Table 15.

Table 14

| Composition of feed: | | | |
|---|---|---|---|
| Crude protein | Crude fat | Crude fiber | Crude ash |
| 16.9 % | 4.4 % | 3.7 % | 5.6 % |

Table 15

| | Classification of test sections: | | | |
|---|---|---|---|---|
| Section | Treated section Section 1 | Control section Section 2 | Treated section Section 3 | Control section Section 4 |
| Additive | 0.5 % PANA | None | 0.5 % PANA | None |

4. Feeding method: Each 6 pigs were raised in a solid floor pen of 2.7 × 2.7 m in area with self-feeding, non-litter and free water-drinking, provided that litters had been used prior to the test.

2. Test results:

As shown in Table 16, the swine of the treated sections were more excellent in growth state and were 11.3 % greater in body weight increase than those of the control sections, and thus the growth promoting effect of the additive PANA was recognized. Further, the state of esophageal area of the stomach of each swine was as set forth in Table 17, and it was confirmed that the addition of 0.5 % PANA is effective for preventing the swine from gastric ulcer.

Table 16

| | Growth state (Average): | |
|---|---|---|
| Section Item | Treated sections Sections 1 and 3 | Control sections Sections 2 and 4 |
| Body weight at the time of initiation of test | 45.0 kg | 45.3 |
| Body weight at the time of completion of test | 91.0 kg | 86.2 |
| Body weight increase during the test period | 46.0 kg | 40.9 |
| Average body weight increase per day | 939 g | 835 |
| Feed conversion ratio | 3.46 % | 3.47 |
| Dressed weight | 60.4 kg | 57.5 |
| Dressing percentage | 66.3 % | 66.7 |

Table 17

| | State of esophageal area of stomach: | |
|---|---|---|
| Section Item | Treated sections | Control sections |
| Normal | 1 | 0 |
| Parakeratosis + | 10 | 4 |
| Parakeratosis ++ | 1 | 6 |
| Lesion Partial erosion | 0 | (4) |
| Erosion | 0 | 1 |
| Ulcer | 0 | 1 |

The classification of the lesions is same as in Experimental Example. Provided that the wording "partial erosion" indicates the case of swine which, despite of their having a lesion of parakeratosis ++, slightly caused a partial decay of pavement epithelium. Accordingly, the number in the parentheses overlaps the number of swine which caused parakeratosis ++.

EXAMPLE 4

1. Test method:

1. Test period: 42 days
2. Test swine: 26 Pigs of about 17 kg in body weight were divided into 4 sections. The strains of the pigs and the classification of the test sections were as set forth in Table 18. All the male piglets were castrated.

Table 18

Strains of piglets and classification of test sections:

| Section 1 | Section 2 | Section 3 | Section 4 |
|---|---|---|---|
| A-31 ♂ | A-34 ♂ | A-36 ♂ | A-35 ♂ |
| A-32 ♂ | A-38 ♂ | A-37 ♂ | A-39 ♂ |
| A-33 ♂ | B-40 ♂ | B-41 ♂ | B-42 ♂ |
| B-43 ♀ | B-44 ♀ | B-46 ♀ | B-45 ♀ |
| B-47 ♀ | C-52 ♂ | C-48 ♂ | C-50 ♂ |
| C-51 ♂ | C-53 ♂ | C-49 ♂ | C-54 ♀ |
| - | C-55 ♀ | C-56 ♀ | - |

Strains:

| | | |
|---|---|---|
| A- | Large Yorkshire ♀ | × Landrace ♂ |
| B- | Large Yorkshire ♀ | × Landrace ♂ |
| C- | Large Yorkshire ♀ | × Landrace ♂ |

3. Feed and Test sections: As the basal feed was used a practical powdery formula feed comprising the same components as in Table 1 of Experimental Example. The composition of the basal feed was as set forth in Table 19, and the classification of the test sections was as set forth in Table 20.

Table 19

| Composition of feed: | | | |
|---|---|---|---|
| Crude protein | Crude fat | Crude fiber | Crude ash |
| 17.6 % | 5.3 % | 2.3 % | 5.4 % |

Table 20

| Section | Classification of test sections: | | | |
|---|---|---|---|---|
| | Treated section Section 1 | Control section Section 2 | Treated section Section 3 | Control section Section 4 |
| Additive | 0.05 % PANA of A.P.D. of 40,000 - 60,000 | None | 0.05 % PANA of A.P.D. of 40,000 - 60,000 | None |

4. Feeding method: Each 6 pigs of the sections 1 and 4 and each 7 pigs of the sections 2 and 3 were individually raised in a solid floor pen of 2.7 × 2.7 m in area with self-feeding, non-litter and free water-drinking.

2. Test results:

The growth state of the pigs of each section was as set forth in Table 21, and the addition of PANA obviously improved the growth state and the feed conversion ratio and inhibited the occurrence of tailbiting.

Table 21

| | Growth state (Average): | |
|---|---|---|
| | Section | |
| Item | Treated sections Sections 1 and 3 | Control sections Sections 2 and 4 |
| Body weight at the time of initiation of test | 16.8 kg | 17.0 |
| Body weight at the time of completion of test | 48.4 kg | 43.9 |
| Body weight increase during the test period | 29.6 kg | 26.9 |
| Feed conversion ratio | 2.60 % | 2.70 |
| Number of piglet caused tail-biting | 0 | 7 |

EXAMPLE 5

1. Test method:
  1. Test period: 21 days
  2. Test swine: 45 Barrows of about 22 kg in body weight were equally divided into 3 sections. The strains of the barrows were the first filial generation of Landrace × Hampshire, and the first filial generation of Landrace × Large Yorkshire of the same litter as above.
  3. Feed and test sections: As the basal feed was used a practical powdery formula feed. The composition of the basal feed and the classification of the test sections were a set forth in Tables 22 and 23, respectively.

Table 22

| Composition of feed: | | | |
|---|---|---|---|
| Crude protein | Crude fat | Crude fiber | Crude ash |
| 15.3 % | 2.9 % | 4.5 % | 5.3 % |

Table 23

| Section | Classification of test sections: | | |
|---|---|---|---|
| | Treated section Section 1 | Treated section Section 2 | Control section Section 3 |
| Additive | 1 % PANA of A.P.D. of 80,000 - 100,000 | 1.5 % PANA of A.P.D. of 80,000 - 100,000 | None |

4. Feeding method: Each 15 barrows were raised in a solid floor pen of 2.7 × 2.7 m in area with self-feeding, non-litter and free water-drinking. The tail of each barrow was docked on the 5th day after birth.

2. Test results:

The growth state of the barrows of each section was as set forth in Table 24, and it is clear that a growth-promoting effect could be attained by addition of 1 % PANA and 1.5 % PANA, repectively.

Table 24

| | Growth state (Average): | | |
|---|---|---|---|
| | Section | | |
| Item | Treated section | | Control section |
| Body weight at the time of initiation of test | 22.2 kg | 22.4 | 22.6 |
| Body weight at the time of completion of test | 39.6 kg | 39.0 | 36.5 |
| Body weight increase during the test period | 17.4 kg | 16.6 | 13.9 |
| Feed conversion ratio | 2.43 % | 2.40 | 2.70 |

Further, the state of esophageal area of stomach was as set forth in Table 25, and a considerable number of barrows having normal stomachs was observed in the treated sections, whereas no barrow having normal stomach was observed at all in the control section.

Table 25

| | State of esophageal area of stomach: | | |
|---|---|---|---|
| | Section | | |
| Item | Treated section | | Control section |
| Normal | | 8 | 10 | 0 |
| Para-kerato-sis + | 7 | 5 | 3 |
| Lesion | Parakeratosis ++ | 0 | 0 | 7 |
| | Erosion | 0 | 0 | 4 |
| | Ulcer | 0 | 0 | 1 |

The classification of the lesions is the same as in Experimental Example.

What is claimed is:

1. A method of preventing gastric ulcer and tail-biting in swine comprising continuously or repeatedly feeding to said swine an effective amount of sodium polyacrylate or potassium polyacrylate having an average polymerization degree of not less than 15,000.

2. The method of claim 1 wherein said sodium polyacrylate or potassium polyacrylate have an average polymerization degree of 15,000 to 100,000.

3. The method of claim 1 wherein said sodium polyacrylate or potassium polyacrylate is fed to said swine as a feed additive in amount of 0.05 to 1.5 % by weight of feed.

* * * * *